United States Patent [19]

Krueger et al.

[11] Patent Number: 5,032,595
[45] Date of Patent: Jul. 16, 1991

[54] METHOD OF STIMULATING STEROIDOGENESIS WITH ALPIDEM

[75] Inventors: Karl E. Krueger, Silver Spring, Md.; Vassilios Papadopoulos, Washington, D.C.

[73] Assignee: FIDIA-Georgetown Institute for the Neurosciences, Washington, D.C.

[21] Appl. No.: 440,808

[22] Filed: Nov. 24, 1989

[51] Int. Cl.$^5$ .................. A61K 31/44; A61K 31/435
[52] U.S. Cl. ........................................................ 514/300
[58] Field of Search ........................................... 514/300

[56] References Cited

U.S. PATENT DOCUMENTS

| | | | |
|---|---|---|---|
| 4,460,592 | 7/1984 | Kaplan et al. | 514/300 |
| 4,808,594 | 2/1989 | George et al. | 514/300 |
| 4,847,263 | 7/1989 | George et al. | 514/300 |

FOREIGN PATENT DOCUMENTS 0050563  4/1982  European Pat. Off. ............ 514/300

*Primary Examiner*—Shep K. Rose
*Attorney, Agent, or Firm*—Birch, Stewart, Kolasch & Birch

[57] ABSTRACT

The present invention is directed to a method of stimulating steroidogenesis in a host by administering a steroidogenesis stimulating effective amount of alpidem, which has the following formula:

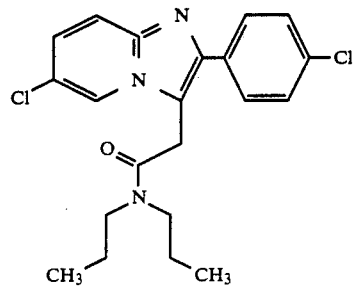

7 Claims, 5 Drawing Sheets

Y-1 CELLS
r = 0.976

MA-10 CELLS
r = 0.970

METHOD OF STIMULATING STEROIDOGENESIS WITH ALPIDEM

FIELD OF THE INVENTION

The present invention is directed to a method of stimulating steroidogenesis in a host by administering a steroidogenesis stimulating effective amount of alpidem.

BACKGROUND OF THE INVENTION

Benzodiazepines are one of the most widely used class of drugs in therapy due to their anxiolytic and anticonvulsant properties. It is now well established that besides their interaction with specific recognition sites located in the brain, benzodiazepines bind to membranes prepared from various tissues containing the so-called peripheral-type benzodiazepine receptor site(s) (PBR). Benzodiazepines have been demonstrated to elicit their primary therapeutic actions in the central nervous system through specific binding sites on GABA-gated chloride channels. PBR are also abundant in neural tissue where they appear to be preferentially associated with astroglial cells.

The central nervous system is also known to synthesize steroids. Steroids have been demonstrated to be potent modulators of $GABA_A$ receptors, implying a physiological role of steroids as regulators of GABAergic transmission.

Heretofore, a certain known compound Ro 5-4864 of the benzodiazepine class was believed to stimulate PBR and as a result androgen production. See Ritta et al, Life Sciences; Vol. 40, pp. 791-798 (1987).

One problem with the benzodiazepine class of compounds in stimulating androgen production is that they, at therapeutic doses, do not selectively stimulate the peripheral-type benzodiazepine receptor, but rather, and as is well known, their primary pharmacological indication is for use as centrally acting anxiolytic or anticonvulsant agents. Another problem associated with the benzodiazepines is that therapeutic doses for stimulating steroidogenesis also stimulate the benzodiazepine receptors in the central nervous system.

Likewise, other agents such as the imidazopyridines have been known to have an affinity for the PBR. Langer et al, Pharmacol. Biochem. and Behavior (1988) Vol. 29 pp. 763-766 discuss the affinity of two imidazopyridines, i.e. zolpidem and alpidem for PBR. This paper is silent as to the use of these compounds for selectively stimulating steroidogenesis or the doses necessary to bring about this stimulation while at the same time minimally stimulating the centrally acting benzodiazepine receptors.

As a result, the present inventors have investigated which compounds would have a high affinity for PBR for stimulating steroidogenesis and yet have a low affinity for the centrally acting benzodiazepine receptors which are responsible for their anxiolytic and anticonvulsant properties.

SUMMARY OF THE INVENTION

The present invention is directed to a method of stimulating steroidogenesis by administering to a host a steroidogenesis stimulating effective amount of alpidem.

Aldipem is a compound of the chemical class of drugs which is known as the imidazopyridines. Alpidem has the following structure:

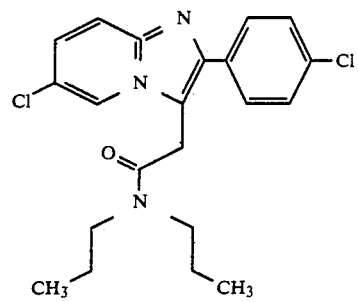

Aldipem can be obtained from Synthelabo Recherche, Paris, France.

By stimulating steroidogenesis, alpidem is useful in the following therapies: disorders of endocrine function following cancer therapy, disorders of the hypothalamic-pituitary-adrenal axis, disorders at the level of peptide hormone receptors, changes in hormone responsiveness due to local regulators, male gonadal dysfunctions, and female gonadal dysfunctions.

DESCRIPTION OF THE PREFERRED EMBODIMENTS

Figure 1A:
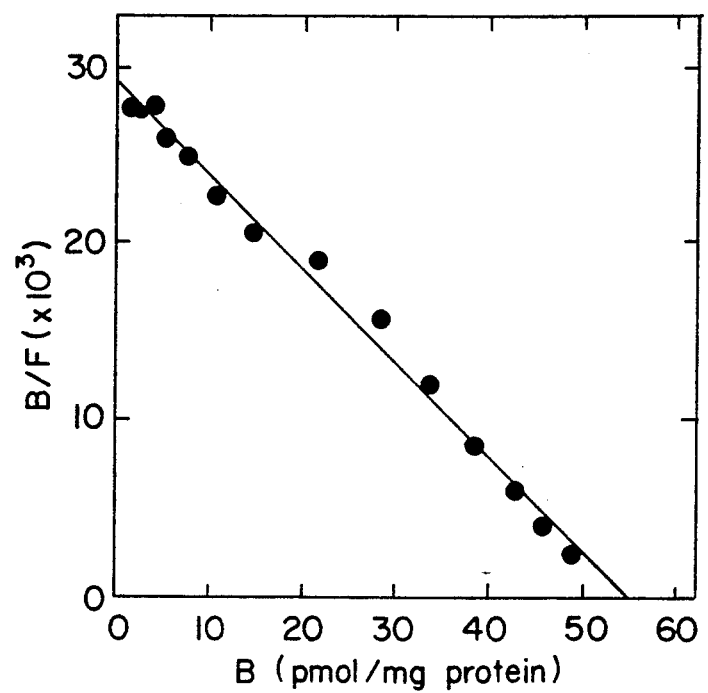
FIG. 1a is a Scatchard analysis of [$^3$H] PK 11195 binding in Y-1 cells.

By stimulating steroidogenesis with alpidem, one can increase steroid production such as androgen production and/or increase estrogen production, or corticosterol production and the like.

The steroidogenesis referred to herein can occur within the central nervous system, including the brain, as well as in the periphery. By periphery is meant that part of the body outside of the central nervous system.

Steroidogenesis can also occur in the adrenal cortex.

With respect to the treatment of disorders of endocrine function following cancer therapies which include hypothalamic/pituitary insufficiency after incidental irradiation for nasopharyngeal/intracranial tumors; adrenal insufficiency in connection with antineoplastic therapy; decreases in estrogen production in chemotherapy treated patients as well as decreases in the levels of the gonadotropins LH and FSH; and decreases in testosterone production in chemotherapy treated patients, alpidem is useful. Treatment with alpidem will bypass the regulatory steps affected by these drugs, and/or therapies.

With respect to the treatment of endocrine disorders of the hypothalamic-pituitary-adrenal axis, those diseases which result in increased or decreased secretion of corticotropin-releasing factor (CRF), adrenocorticotropic hormone (ACTH), or cortisol, and the like, as well as from congenital defects in steroid biosynthesis, can also be treated. Adrenalcortical disorders can result from the primary disorder of the adrenal gland secondary to hypothalamic-pituitary disease. Originally treatment of such disorders involved acute and/or long-term steroid replacement therapy. However, steroid replacement therapy is associated with numerous untoward side effects. Treatment with alpidem will diminish the untoward side effects associated with steroid replacement therapy.

With respect to the treatment of disorders at the level of peptide hormone receptors, one of the potential sites of disordered function of the endocrine system is the plasma membrane receptor for the peptide hormone which regulates it. This is the first step leading to the activation of the second and third messenger systems up to the final step, which is the transport of cholesterol from its intracellular stores into mitochondria (the rate-limiting step of steroidogenesis) and subsequently the biosynthesis of steroids. Alpidem increases steroid biosynthesis by bypassing the membrane receptor as well as the second and third messenger systems. Use of this drug will overcome any failures in the above mentioned systems and will maintain steroid production, at physiological levels, in patients presenting with these types of disorders. Also with respect to the treatment of disorders at the level of peptide hormone receptors, those diseases which produce antibodies that block gonadotropin receptors, i.e., autoimmune reproductive organ diseases such as myasthenia gravis, Graves Disease can also be treated with alpidem.

With respect to the treatment of disorders of male gonadal dysfunction, alpidem may be used in all conditions where increased testosterone production is required in order to maintain spermatogenesis and/or for the formation and maintenance of the secondary sexual characteristics. Examples of such conditions include primary and secondary hypogonadotrophic hypogonadism, prenatal hypoandrogenism, postnatal prepubertal androgen deficiency, juvenile hypoandrogenism, and disorders affecting the male secondary sexual characteristics.

With respect to the treatment of disorders of female gonadal dysfunction, one application of alpidem will be in connection with luteal insufficiency syndrome. It is known that luteal progesterone secretion is paramount for the maintenance of pregnancy during the first 10-14 weeks until the placenta begins producing steroids In the case of luteal insufficiency the corpus luteum does not produce enough progesterone to maintain pregnancy. Alpidem therapy may also be used to supplement or increase progesterone biosynthesis and production to levels which are similar to those required for maintaining a normal pregnancy. Alpidem may also be used to increase the steroid production in aged women when stromal and endometrial cell proliferation is required.

Pharmaceutical Compositions

In order to carry out the method of the present invention, alpidem may be made into pharmaceutical compositions by combination with appropriate medical carriers or diluents, and may be formulated into preparations in solid, semisolid, liquid, etc., form, such as tablets, capsules, powders, granules, ointments, solutions, suppositories, or injections in the usual ways for oral or parenteral administration. The following methods and excipients are merely exemplary and are in no way limiting.

In the pharmaceutical dosage forms, alpidem may be used in the form of its pharmaceutically acceptable salts, and also may be used alone or in appropriate association, as well as in combination with other pharmaceutically active compounds.

In the case of oral preparations, alpidem may be used alone or combined with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Furthermore, alpidem may be made into suppositories by mixing with a variety of bases such as emulsifying bases or water-soluble bases.

Alpidem may be formulated into preparations for injections by dissolving, suspending or emulsifying them in aqueous solvents such as normal saline, Dextrose 5%, or a non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers, preservatives, etc.

The dose of alpidem varies with the subject, drug form, method and period of administration. However, in order to obtain desirable effects, generally it is recommended to administer 0.01 mg to 0.5 mg/kg body weight of alpidem. The dosing can range from one to six times per day. In terms of composition, alpidem should be present between 0.1 to 100% by weight.

PHARMACOLOGICAL STUDIES

Dosing Studies

Alpidem was suspended in isotonic saline by sonication and administered intravenously to adult Sprague-Dawley rats (200-300 g). The doses used ranged from 0.01-1.5 mg/kg, the highest concentration being just below the level needed for behavioral effects to be observed. Control rats were injected with saline alone to serve as control for measurement of basal serum levels of testosterone. After specific times the rats were killed by decapitation and blood was collected. Serum was prepared and testosterone was measured by radioimmunoassay. Each point included three rats for all permutations of each time point and concentration of alpidem used.

At doses greater than or equal to 0.01 mg/kg alpidem was found to cause a significant increase in serum testosterone levels to an extent of 2-4 times above control levels. Elevated testosterone levels were maintained for at least 4 hours after which the increased steroid levels became lesser in magnitude. This experiment was conducted at least five times with similar results.

For ease of graphical analysis, the following abbreviations depict the compounds which were utilized in the following pharmacological studies:

♦ = alpidem
△ = PK 11195 (1-(2-chlorophenyl)-N-methyl-N-(1-methylpropyl)-3-isoquinoline carboxamide)
● = PK 14067 = (-) N,N-dimethyl-x-methyl-2-phenyl-4-quinoline propanamide
□ = 4'-chlorodiazepan
◇ = zolpidem
○ = PK 14068 = (+) N,N-dimethyl-x-methyl-2-phenyl-4-quinoline propanamide
■ = diazepan
▲ = flunitrazepan
X = clonazepan
* = flunazenil

EXPERIMENT I

Methods

Cells—The Y-1 adrenal mouse tumor cell line used in these studies was obtained from the American Type Culture Collection (ATCC #CCL 79). Stock cultures were grown in modified Waymouth's MB752/1 medium containing 20 mM HEPES, 1.2 g/l $NaHCO_3$, 15% horse serum and 2.5% fetal calf serum, pH 7.4. Before use the cells were washed three times at 30 min intervals, with serum-free media in order to eliminate serum components that may interfere with the assays and were incubated for the indicated time periods in the presence of the drugs under investigation. Bovine fasciculata-reticularis and adrenocortical cells from adult (300 g) Sprague-Dawley rats were prepared as previously described by Yanagibashi et al, (1989) Endocrinology 124; 2838-2391.

Radioligand binding assays—Y-1 cell cultures were scraped from the flasks (75 $mm^2$) in 5 ml of Kreb's buffer, dispersed by repetitive pipetting, and centrifuged at 1,200 × g for 5 min. The cell pellets were resuspended in Kreb's buffer and larger cellular aggregates were allowed to settle for 5 min. The finely dispersed cell suspensions were taken for further experimentation.

Binding assays were performed in a total volume of 250-400 ul of Kreb's buffer containing [$^3$H]PK 11195 (0.07-20 nM) with 5 ug of cellular protein. Incubations were conducted at 37° C. for 30 min and bound radioligand was measured by filtration through Whatman GF/C filters followed by four rapid 5 ml washes with 25 mM Tris-HCl (pH 7.4) containing 1 uM PK 11195. Filters were subjected to liquid scintillation counting. Nonspecific binding was measured in the presence (of 10 uM nonradioactive PK 11195.

Measurement of steroid production—These experiments were performed with the Y-1 cells plated in 12—22 mm wells and incubated for the times shown at a final volume of 1 ml of serum-free media at 37° C. At the end of the incubation period the cell media were saved, centrifuged at 1,500 × g for 10 min, and stored at −20° C. until use. Steroid production was determined by measuring 20-γ-hydroxyprogesterone, the main steroid product of these cells, using a radioimmunoassay with an antibody donated by Dr. G. Nieswender (Univ. of Colorado, Fort Collins), under the process described in Kowal J. (1970), Recent Progress in Hormone Research 26, 623-687 and Schimmer B.P. (1981) in Functionally Differentiated Cell Lines, ed. Sato G. (Alan R. Liss, Inc., New York, N.Y.), pp 61-92. Cortisol and corticosterone, indices for steroid production in bovine and rat adrenocortical preparations, respectively, were also measured by radioimmunoassay using commercially obtained kits (Baxter Scientific Products, McGaw Park, Ill. and Endocrine Sciences, Tarzana, Calif., respectively). Analysis of the radioimmunoassay data was performed using the "IBM-PC RIA DATA REDUCTION" program (version 4.1) obtained from Jaffe and Assoc. (Silver Spring, Md).

Protein measurements—Protein was quantitated by the method of Bradford (1976) Anal. Biochem. 72, 248-254 using bovine serum albumin as a standard.

RESULTS

Binding of tested compounds in Y-1 cells: Measurement of [$^3$H]PK 11195 binding in Y-1 adrenocortical cells at 37° C. demonstrated rapid association kinetics reaching equilibrium within 15 min. which was stable for at least two hours and fully reversible by adding excess PK 11195. Scatchard analysis of [$^3$H]PK 11195 binding in Y-1 adrenocortical cells revealed a single class of recognition sites with a dissociation constant of 1.8 nM and a $B_{max}$ of 54 pmol/mg of protein as seen in FIG. 1a. The high density of PBR in total cell membranes is consistent with the abundance previously reported in rat adrenal mitochondrial preparations, Antkiewicz-Michaluk L. et al. (1988) Mol. Pharmacol. 34, 272-278.

Figure 2A:
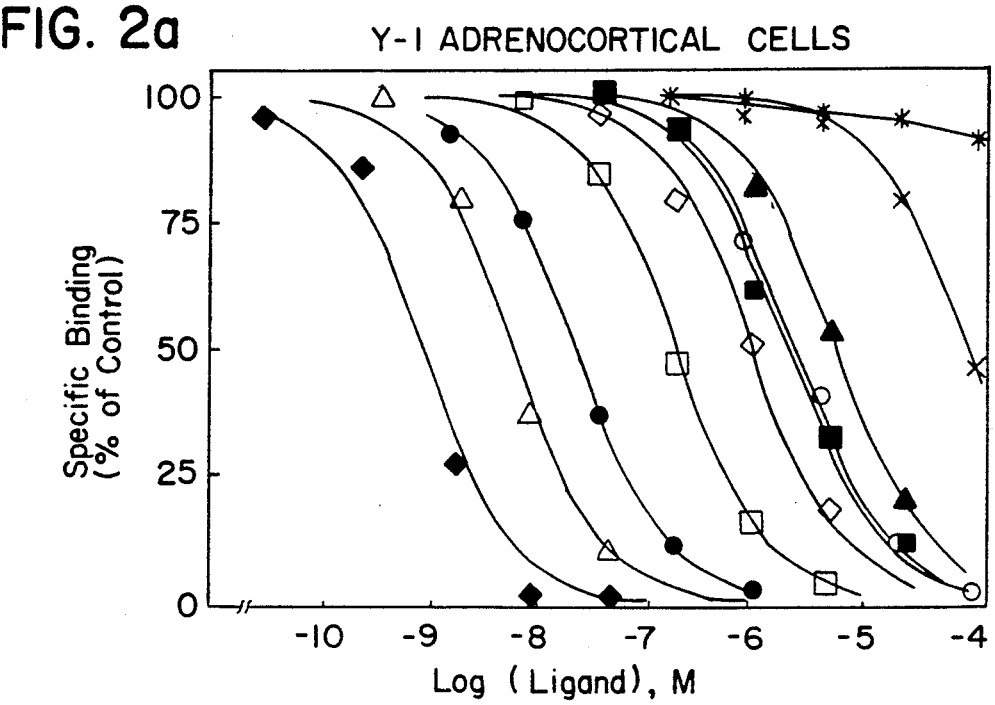
FIG. 2a discloses displacement of specific [$^3$H]PK 11195 binding in Y-1 adrenocortical cells.

Ten different compounds, exhibiting a range of greater than four orders of magnitude in their affinities for PBR, were examined for their potencies to inhibit [$^3$H]PK 11195 binding to Y-1 cells at 37° C. as seen in FIG. 2a. These compounds demonstrated a rank order of compound displacement potency (alpidem > PK 11195 > PK 14067 > 4'-chlorodiazepam > zolpidem > PK 14608, diazepam > flunitrazepam > clonazepam > flumazenil) which is consistent with previous reports studying PBR from rat tissues, Hirsch J. D. et al. (1989) Mol. Pharmacol. 35, 164–172.

Figure 3A:
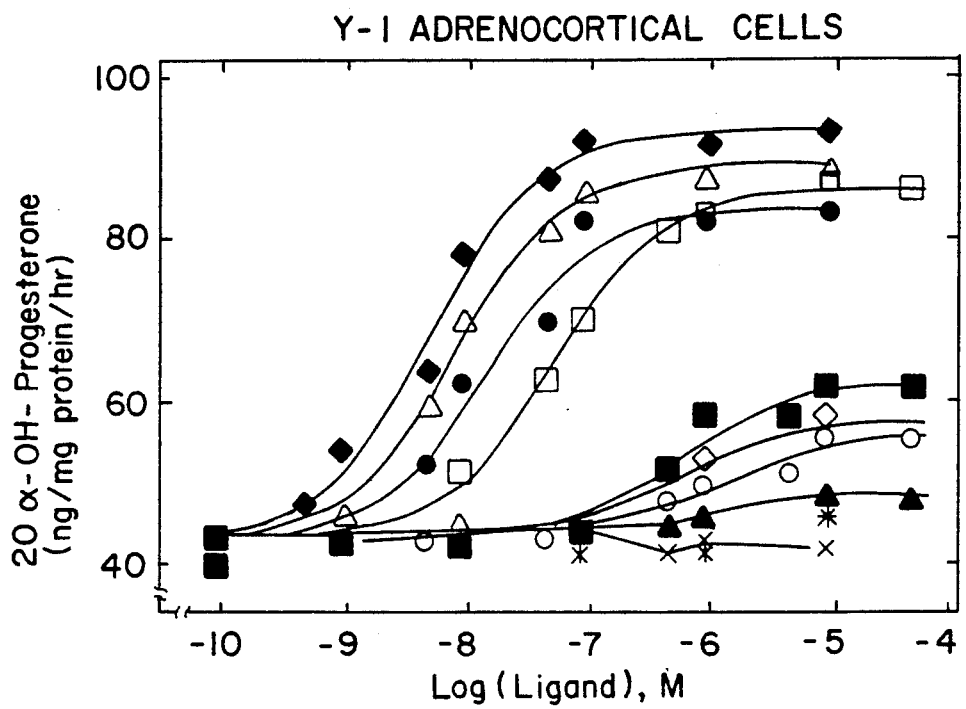
FIG. 3a discloses that the test compounds stimulate steroid biosynthesis as shown by the secretion levels of 20 —OH-progesterone in Y-1 adrenocortical cells.
Figure 3B:
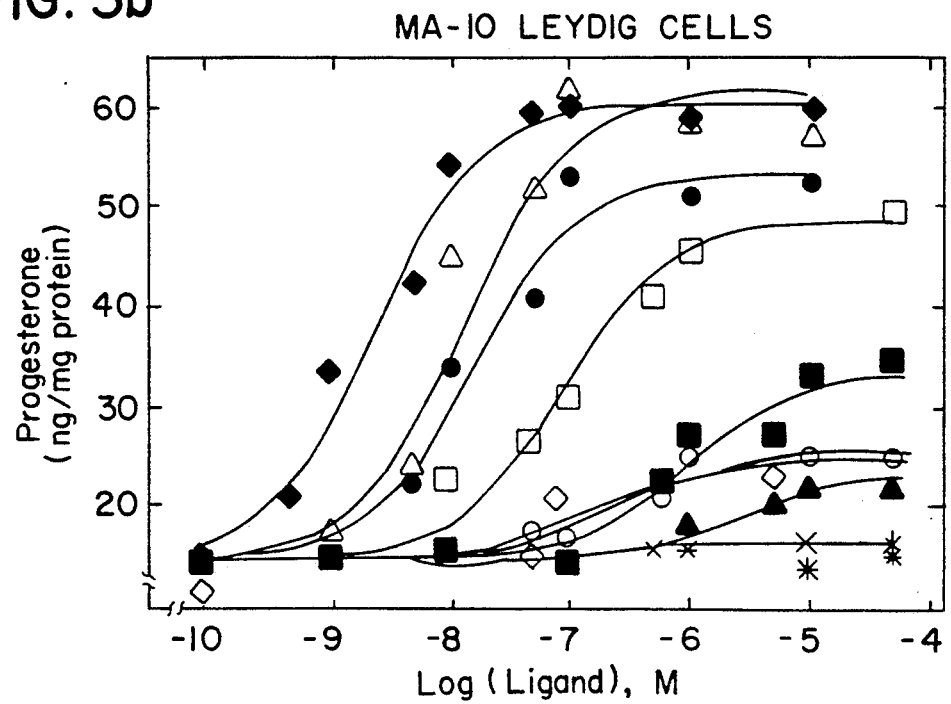
FIG. 3b discloses that the test compounds stimulate steroid biosynthesis as shown by the secretion levels of progesterone in MA-10 Leydig cells.
Figure 4A:
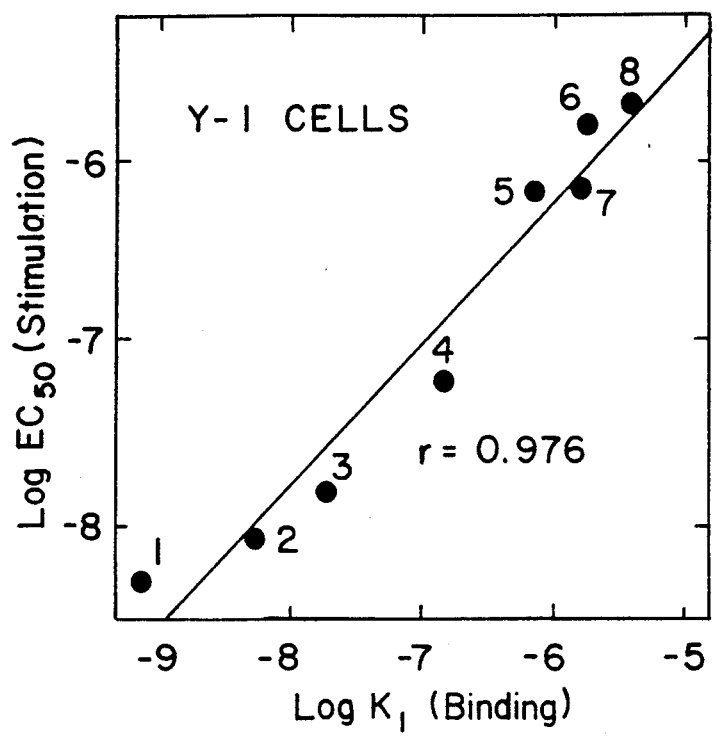
FIG. 4a discloses the correlation of the test compounds between the affinity for PBR and their potency to stimulate steroidogenesis in Y-1 cells (1, alpidem; 2, PK 11195; 3, PK 14067; 4, Ro5-4864; 5, zolpidem; 6, PK 14068; 7, diazepam; 8, flunitrazepam).

Stimulation of steroidogenesis by test compounds. Each compound was tested for its effects in Y-1 cells on secretion of 20-γ-hydroxyprogesterone, the final product in the pathway of steroid synthesis in Y-1 cells. All four compounds which exhibited high potencies in displacing [$^3$H]PK 11195 binding (K <200 nM) stimulated steroid secretion in a concentration-dependent manner, each exhibiting a maximal stimulation of about 2-fold greater than the basal level of steroid secretion (FIG. 3a). In contrast, clonazepam and flumazenil failed to stimulate steroid production while the remaining four compounds stimulated steroid secretion. The maximal stimulation achieved was only 20–50% above the basal levels. When the inhibitory constants of this series of compounds to compete against [$^3$H]PK 11195 binding were compared with their potencies to stimulate steroid secretion (FIG. 4a) an excellent correlation was found (r=0.976) suggesting a direct relationship between compound occupancy of PBR and steroidogenic activity.

Figure 5A:
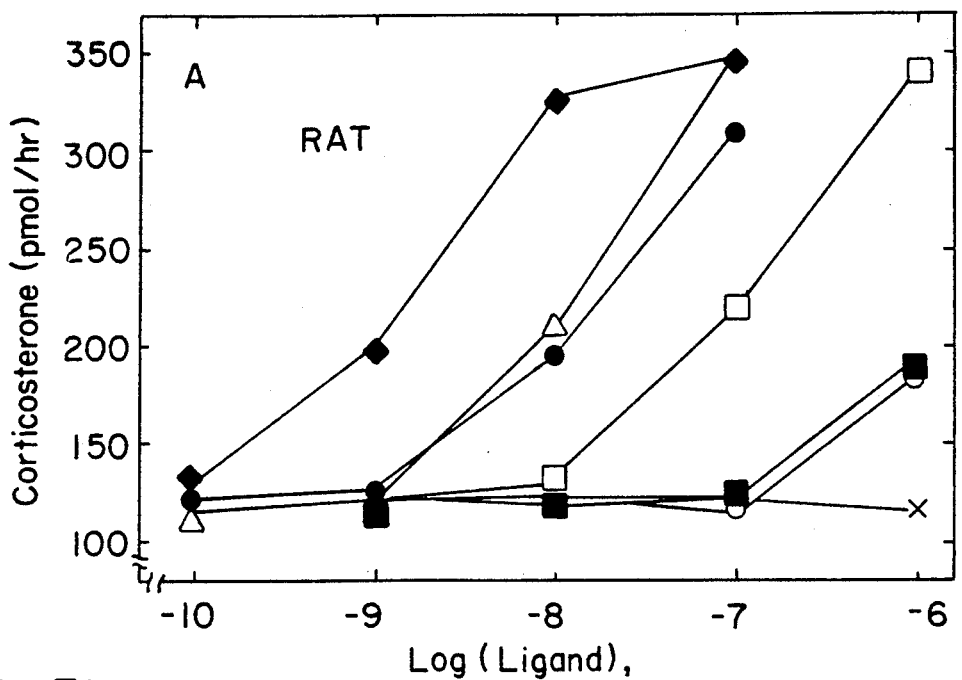
FIG. 5a discloses the stimulation of corticosterone in rat adrenocortical tissue.
Figure 5B:
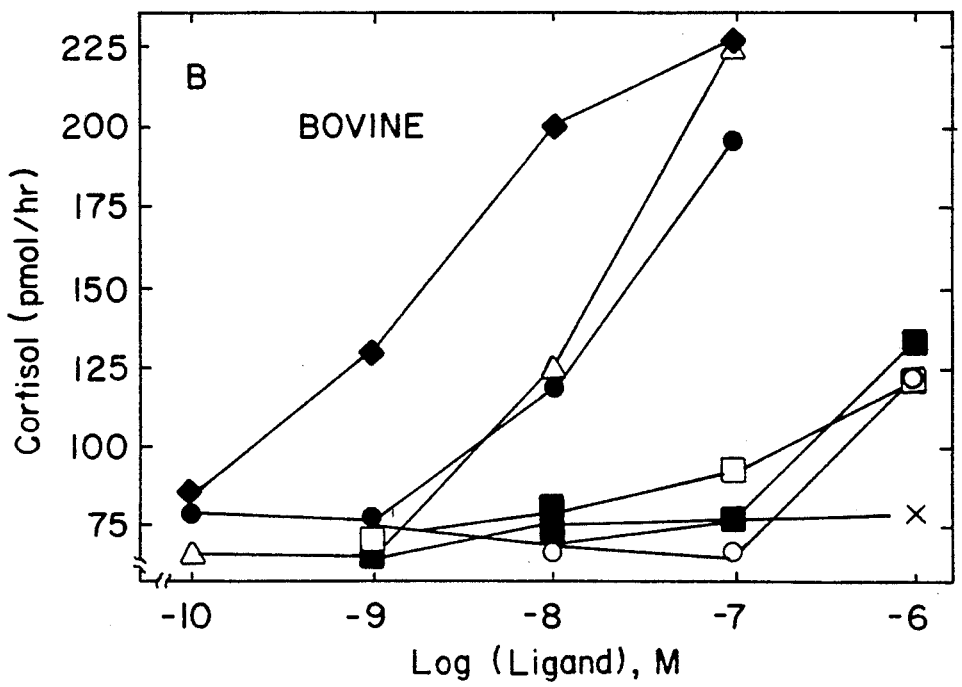
FIG. 5b discloses the stimulation of cortisol in bovine adrenocortical tissue.

Stimulation of steroidogenesis in normal adrenocortical cells. Several of the compounds were also tested for corticosterone and cortisol secretion in dissociated rat and bovine adrenal cortical tissue, respectively. These experiments demonstrate that these high affinity PBR compounds stimulate steroid production in suspensions of adrenocortical cells as well (FIGS. 5a and 5b). Hence, the Y-1 cell line is proven to be a reliable and convenient model system for studying the effects of PBR on steroidogenesis and that the effects observed are likely to be found in vivo as well.

It should also be noted in FIGS. 5a and 5b that 4'-chlorodiazepam is much more potent at stimulating steroidogenesis in rat adrenocortical cells when compared with bovine preparations. This observation is agreeable with the species-dependent differences described for the binding of 4'-chlorodiazepam to PBR as described in Awad et al (1987) J. Neurochem. 49, 1407-1414. Therefore, this experiment provides additional support that steroidogenesis is specifically mediated by interaction of the compound with PBR rather than by another mechanism elicited by the compound.

EXPERIMENT II

Cells—The MA-10 cell line originally cloned from the solid M5480P mouse Leydig cell tumor used in these experiments was obtained from Dr. Mario Ascoli (The Population Council, Rockefeller University, N.Y.). Stock cultures were grown in modified Waymouth's MB752/1 medium containing 20 mM HEPES, 1.2 g/l NaHCO3 and 15% horse serum, pH 7.4 as described by Ascoli (1981) Endocrinology 108, 88-95. Before use, the MA-10 Leydig cells were washed three times, in 30 min intervals, with serum-free media in order to eliminate serum components that may interfere with the assays and incubated for the indicated periods of time in the presence of the indicated substances. Testicular interstitial cells were prepared by enzymatic dissociation of testes obtained from adult Sprague-Dawley (300 g) rats. This preparation contained 20-30% 3$\beta$-hydroxysteroid dehydrogenase positive cells (Leydig cells). Leydig cells were further purified using discontinuous Percoll gradient centrifugation as described by Papadopoulos et al., 1985 FEBS Letters 188, 312-316. The preparations obtained contained 75-85% Leydig cells as shown by the histochemical staining for 3$\beta$-hydroxysteroid dehydrogenase by the procedure of Papadopoulos et al., FEBS Letters 188, supra. [$^3$H]PK 11195 binding assays—Cells were scraped from 75 cm$^2$ culture flasks into 5 ml of Kreb's buffer, dispersed by trituration, and centrifuged at 1,200 × g for 5 min. The cell pellets were resuspended in buffer and larger cell aggregates were allowed to settle to the bottom of the tube before the cell suspension was retrieved for experimentation.

[$^3$H]PK 11195 binding studies on 5 ug of protein from the cell suspensions were performed in 250-400$\mu$l of Kreb's buffer at 37° C., essentially the same conditions under which the effects of the compounds on steroidogenesis were studied. Nonspecific binding was determined in the presence of 10 $\mu$M PK 11195. After 30 min the assays were stopped by filtration through Whatman GF/C filters and washed with 20 ml of 25 mM Tris-HCl (pH 7.4) containing 1 $\mu$M PK 11195. Radioactivity trapped on the filters was determined by liquid scintillation counting. Total binding accounted for less than 10% of the radioligand introduced while specific binding was >85% of the total binding at all radioligand concentrations used.

Steroid Biosynthesis—These experiments were performed with the MA-10 Leydig cells plated in 12×22 mm wells and incubated for the times shown and in the presence of the indicated substances at a final volume of 1 ml of serum-free media at 37° C. Where purified rat Leydig cells were used, 50,000 cells per 500 ul of serum-free media were incubated in borosilicate culture tubes at 32° C. At the end of the incubation period the cell media were saved, centrifuged at 1500 × g for 10 min, and stored at −20° C. until use. Cells were dissolved with 0.1 N NaOH for protein measurement.

Progesterone and 20-$\gamma$-hydroxyprogesterone production for the MA-10 cells, and testosterone accumulation for the rat Leydig cells were measured by means of radioimmunoassay. Antibody to progesterone was obtained from Endocrine Sciences (Tarzana, Calif.) and the assay was performed as described by the manufacturer. Antibody to 20-$\gamma$-hydroxyprogesterone was obtained from the University of Colorado and the assay was performed as described by Resko (1971) Endocrinology 33, 940-948. Anti-testosterone antibody was obtained from ICN Co. (Lisle, Ill.), and the assay was performed as described by the manufacturer. Analysis of the radioimmunoassay data was performed using the "IBM-PC RIA Data Reduction" program (version 4.1) obtained from Jaffe and Assoc. (Silver Spring, Md).

Protein measurement—Protein was measured by the method of Bradford M. M. (1976) Anal. Biochem. 72, 248-254, using bovine serum albumin as a standard.

Materials—Purified human Chorionic Gonadotropin (hCG; batch CR-125 of biological potency 11900 IU/mg) was obtained from the National Institutes of Health. Purified mouse Epidermal Growth Factor (mEGF) was obtained from Sigma Chemical Co. [1,2,6,7$^3$H(N)]progesterone (sp. act. 94.1 Ci/mmol), 20-[1,2$^3$H(N)]hydroxyprogesterone (sp.act. 45 Ci/mmol) [1,2,6,7$^3$H(N)]testosterone (sp. act. 93.9 Ci/mmol), [7$^3$H(N)]pregnenolone (sp. act. 22.6 Ci/mmol) and [N-methyl-$^3$H]PK 11195 were obtained from Du Pont-New England Nuclear. [3H]PK 14105 was obtained from Research Products International Corp., Mt. Prospect, Illinois. PK 11195, PK 14067, and PK 14068 were obtained from Pharmuka Lab. Groupe Rhone Poulenc Sante, Gennevilliers, France. Zolpidem and alpidem were obtained from Synthelabo Recherche, Paris, France. Diazepam, clonazepam, flumazenil, and Ro5-4864 were obtained from Hoffman-LaRoche (Nutley, N.J.). Aminoglutethimide was obtained from Ciba-Geigy (Summit, N.J.) and Trilostane from Sterling-Winthrop (New York, N.Y.). Percoll was obtained from Pharmacia (Piscataway, N.J.). All cell culture supplies were obtained from GIBCO and cell culture plasticware was obtained from Corning Glass (Corning, N.Y.). All other chemicals were of analytical quality and were obtained from readily available commercial sources.

Figure 1B:
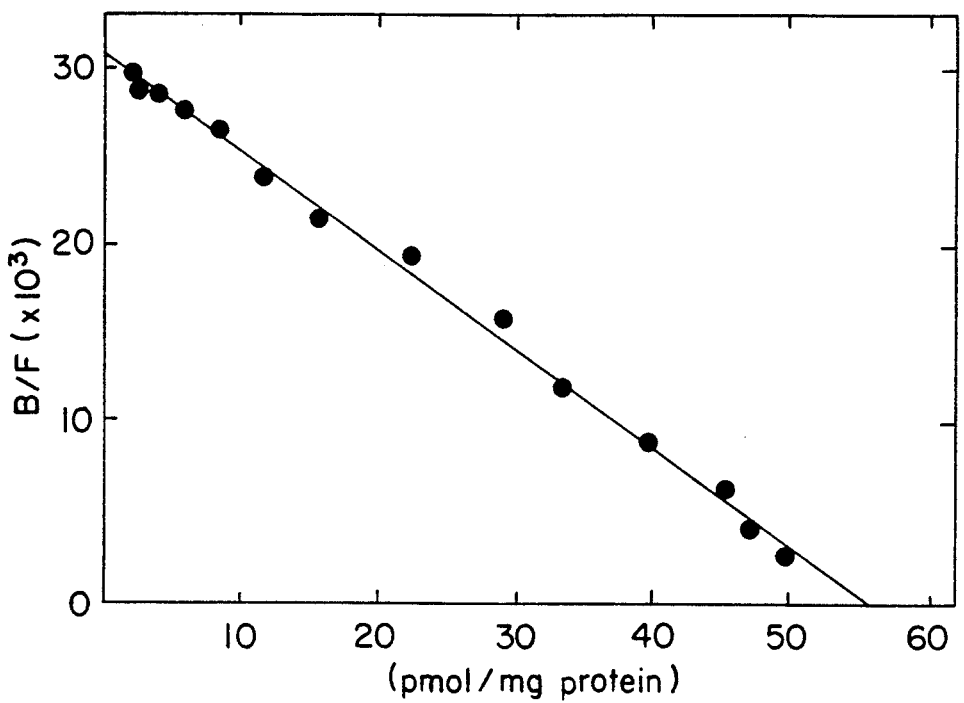
FIG. 1b is a Scatchard analysis of [$^3$H]PK 11195 binding in MA-10 Leydig cells in the concentration range of 0.07-20 nM.

Characterization of PBR in MA-10 cells—Kinetics of [$^3$H]PK 11195 binding at 37.C to MA-10 cells revealed that specific binding of this compound was rapid reaching steady-state conditions after 10 min. Furthermore, if 10 uM PK 11195 was subsequently added, specific radioligand binding was completely displaced within 15-20 min. As can be seen by FIG. 1b, scatchard analysis demonstrated a single class of binding sites with a dissociation constant of 1.8 nM at a density of 56 pmol/mg of protein.

Figure 2B:
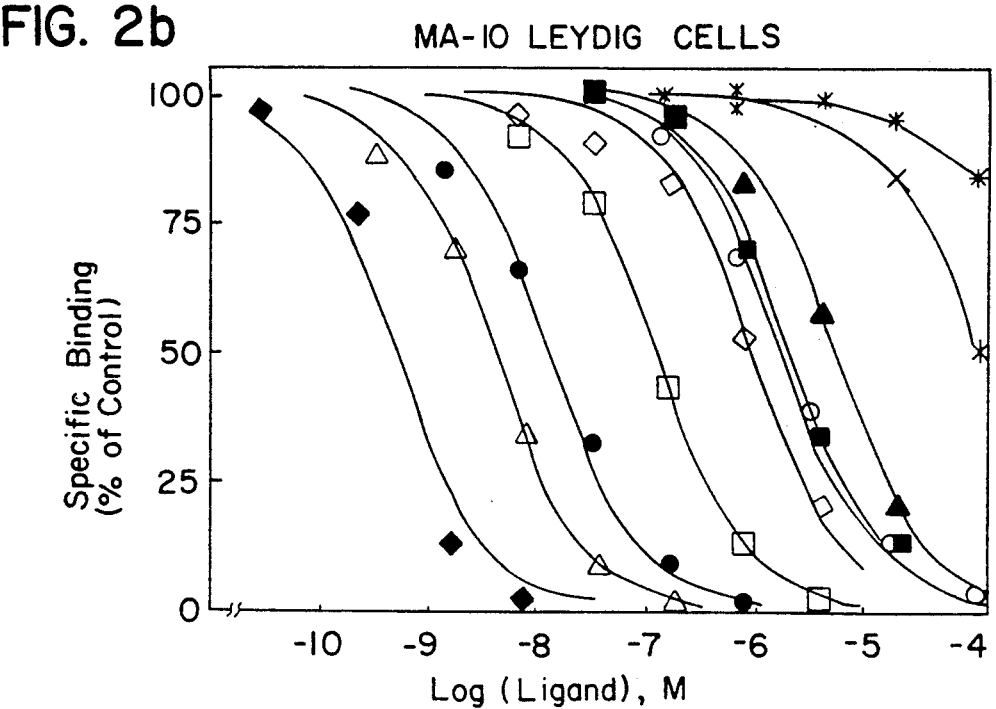
FIG. 2b discloses the displacement of specific [$^3$H]PK 11195 binding in MA-10 Leydig cells.

Specificity of these binding sites was determined using ten different compounds from several classes of organic compounds known to interact with PBR. As shown in FIG. 2b, these compounds exhibited a rank order potency to compete against [$^3$H]PK 11195 binding.

Figure 4B:
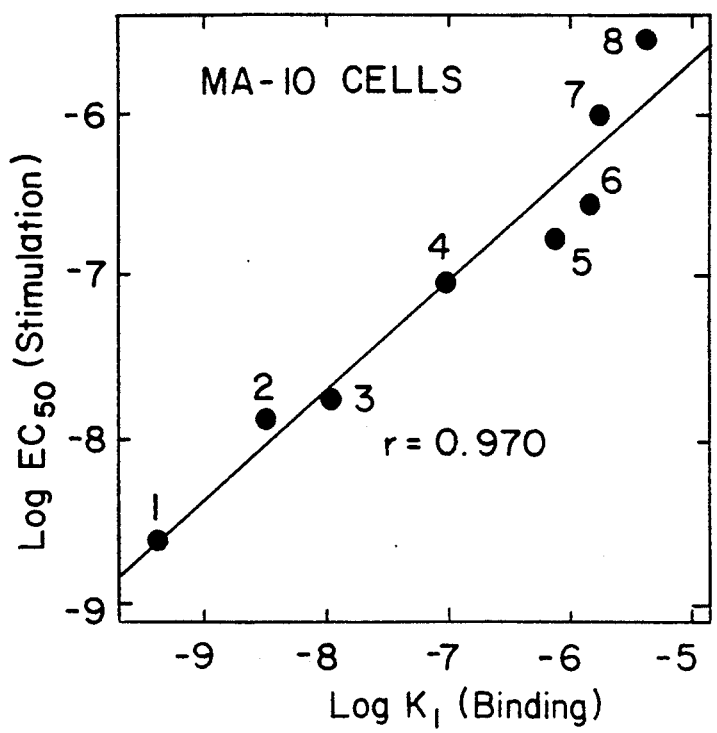
FIG. 4b discloses the correlation of the test compounds between affinity for PBR and their potency to stimulate steroidogenesis in MA-10 cells (1, alpidem; 2, PK 11195; 3, PK 14067; 4, Ro5-4864; 5, zolpidem; 6, PK 14068; 7, diazepam; 8, flunitrazepam).

Effect of PBR compounds on MA-10 Leydig cell steroid biosynthesis—In order to investigate whether the compounds affected Leydig cell steroidogenesis, increasing concentrations of the compounds were incubated for 4 hours with MA-10 cells and their effects on progesterone production were measured (FIG. 4b). The three most potent compounds of this series were very efficacious at stimulating progesterone synthesis while the less potent compounds achieved either a lower level of maximal stimulation or did not have an effect on steroid production. Alpidem, PK 11195 and PK 14067 were the most potent of the tested compounds and produced a 3 to 4-fold stimulation of progesterone production.

Comparing the EC$_{50}$'s of the stimulatory effect of the different compounds with the inhibitory constants with which these compounds compete for [$^3$H]PK 11195 binding to the MA-10 cells (FIG. 4b), an excellent correlation was observed (r=0.970). This provides strong evidence that the effects of these compounds on steroidogenesis is a consequence of their 5 binding to PBR.

Regulation of steroidogenesis by PBR compounds in Leydig cells purified from rat testis—The action of these compounds on purified rat Leydig cell steroidogenesis was also examined. Table I shows that alpidem, PK 11195 and Ro5-4864 stimulate by about 2-fold testosterone production by purified rat Leydig cells while diazepam was less potent and clonazepam had no effect.

TABLE I

Effects of PBR Compounds on Basal and hCG Stimulated Rat Leydig Cell Steroidogenesis

| Treatment | Testosterone ng/10$^5$ cel s/4 hours | |
|---|---|---|
| | No Additions | hCG (50 ng/ml) |
| Control | 1.30 ± 0.20 | 15.13 ± 2.05 |
| Alpidem (10$^{-7}$M) | 2.35 ± 0.27 | 15.02 ± 2.31 |
| PK 11195 (10$^{-6}$M) | 2.33 ± 0.21 | 14.86 ± 1.51 |
| PK 14607 (10$^{-6}$M) | 2.20 ± 0.30 | 14.13 ± 1.49 |
| PK 14608 (10$^{-5}$M) | 1.16 ± 0.15 | 13.50 ± 1.51 |
| Ro5-4864 (10$^{-5}$M) | 2.40 ± 0.30 | 14.10 ± 2.26 |
| Diazepam (10$^{-5}$M) | 1.90 ± 0.10 | 14.96 ± 3.09 |
| Clonazepam (10$^{-5}$M) | 1.16 ± 0.11 | 14.90 ± 2.22 |

Purified rat Leydig cells were incubated with the indicated additions for 4 hours at 32° C. Testosterone was measured by radioimmunoassay. Results of a representative experiment are shown as conducted in triplicate assays. Mean ± S.D. values (n = 3) are given.

Moreover, stimulation of rat Leydig cell steroidogenesis was stereoselective for PBR as demonstrated using the optical isomers PK 14067 and PK 14068. The hCG-stimulated testosterone production was not affected by these compounds as shown in Table I. These results verify that the effects on steroidogenesis mediated by PBR are also found in normal rat Leydig cell preparations. Hence, the MA-10 cell line has proven to be a suitable model system to examine the role of PBR in Leydig cell function.

Having thus described the invention, it is to be noted that the same can be varied without departing from the spirit and scope thereof, and all such variations are intended to be included within the scope of the following claims.

We claim:

1. A method of stimulating steroidogenesis by administering to a host in need thereof a steroidogenesis stimulating effective amount of alpidem.

2. The method according to claim 1, wherein said steroidogenesis effective amount is 0.01 to 0.5 mg/kg body weight.

3. The method according to claim 1, wherein said steroidogenesis comprises androgen production.

4. The method according to claim 1, wherein said steroidogenesis comprises estrogen production.

5. The method according to claim 1, wherein said steroidogenesis comprises steroidogenesis in the central nervous system.

6. The method according to claim 1, wherein said steroidogenesis comprises steroidogenesis outside of the central nervous system.

7. The method according to claim 1, wherein said steroidogenesis comprises steroidogenesis the adrenal cortex.

* * * * *